US008734858B2

(12) United States Patent
Popovici et al.

(10) Patent No.: US 8,734,858 B2
(45) Date of Patent: May 27, 2014

(54) USE OF A MYRICA GALE PLANT FOR PRODUCING A HERBICIDE AGENT

(75) Inventors: Jean Popovici, Lyons (FR); Cédric Bertrand, Coufouleux (FR); Gilles Comte, Villefontaine (FR)

(73) Assignees: Universite Claude Bernard Lyon I, Villeurbanne Cedex (FR); Centre National de la Recherche Scientifique, Paris Cedex (FR)

( * ) Notice: Subject to any disclaimer, the term of this patent is extended or adjusted under 35 U.S.C. 154(b) by 426 days.

(21) Appl. No.: 13/055,944

(22) PCT Filed: Jul. 27, 2009

(86) PCT No.: PCT/FR2009/051507
§ 371 (c)(1),
(2), (4) Date: Apr. 6, 2011

(87) PCT Pub. No.: WO2010/012945
PCT Pub. Date: Feb. 4, 2010

(65) Prior Publication Data
US 2011/0201503 A1 Aug. 18, 2011

(30) Foreign Application Priority Data
Jul. 28, 2008 (FR) ...................................... 08 55166

(51) Int. Cl.
*A01N 65/00* (2009.01)
*A61K 36/45* (2006.01)
*A01N 25/26* (2006.01)
*A01N 43/02* (2006.01)
*A01N 43/16* (2006.01)
*A01N 35/00* (2006.01)

(52) U.S. Cl.
USPC ........... 424/725; 424/732; 504/100; 504/140; 504/292; 504/348

(58) Field of Classification Search
CPC ....... A01N 25/00; A01N 31/00; A01N 31/04; A01N 31/06; A01N 31/16; A01N 35/06; A01N 65/00; A01N 65/08; A01N 65/16
See application file for complete search history.

(56) References Cited

U.S. PATENT DOCUMENTS 4,106,926 A * 8/1978 Thomas ........................ 504/322
4,309,207 A * 1/1982 Devlin .......................... 504/174

FOREIGN PATENT DOCUMENTS

GB 2 224 934 5/1990
GB 2 362 574 11/2001

OTHER PUBLICATIONS

Rhode Island Coastal Plant Guide, Morella(Myrica) pensylvanica Baybery 1997-2001.*
WebMD, Best Skin Tighteners, 2005-2013.*
Sweet Gale Definition, 2013.*
Hufford, Charles D. et al., "New dihyddrochalcones . . . Uvaria angolensis", Journal of Natural Products, 45(3), 337-42 CODEN: JNPRDF; ISSN: 0163-3864, 1982 XP002514648 le document en entier.
Misirlioglu, Huriye et al., ".beta.-Tricarbonyl compounds. Part 3. Synthesis of dihydrochalcones of *Myrica gale*", Phytochemistry (Elsevier), 17(11), 2015-19 CODEN: PYTCAS; ISSN: 0031-9422, 1978, XP002514649 "experimental".
Eriksson O. and Bremer B. 1992, Pollination systems, dispersal modes, life forms, and diversification rates in angiosperm families. Evolution 46: 333.
R.L. 1994, The Myricaceae of the United States and Canada: genera, subgenera, and series. SIDA 16: 93-107.
Gleason H.A. and Cronquist A. 1991, Manual of vascular plants of northeastern United States and adjacent Canada. $2^{nd}$ Edition. New York Botanical Garden, Bronx, pp. 80-81 in particular.
Huguet V. Gouy M. Normand P. Zimpfer J.F. and Fernandez M.P. 2005, Molecular Phylogeny of Myricaceae: a reexamination of host-symbiont specificity. Molec. Phylo. Evol. 34: 557-568.
Sylvestre M. Legault J. Dufour D. and Pichette A. 2005, Chemical composition and anticancer activity of leaf essential oil of *Myrica gale* L. Phytomedicine 12: 299-304.
Svoboda K.P. Inglis A. Hampson J. Galambosi B. Asakawa Y. 1998, Biomass production, essential oil yield and composition of *Myrica gale* L. harvested from wild populations in Scotland and Finland. Flav. Frag. 13: 367-372.
Bremness, L. (Ed) 1996 L'oeil Nature: Les plantes aromatiques et médicinales [Nature's eye: Aromatic and medicinal plants]. Bordas, Paris).
Svoboda et al., 1998; Jaenson T.G.T. Palsson K. and Borg-Karlson A.K. 2005 Evaluation of extracts and oils of tick-repellent plants from Sweden Med. Vet. Entomol. 19: 345-352.
Behre, K.E. 1999 the history of beer additives in Europe—a review. Vegetation History and Archaeobotany, 8, 35-48.

* cited by examiner

*Primary Examiner* — Alton Pryor
(74) *Attorney, Agent, or Firm* — Clark & Brody (57) ABSTRACT

The invention relates to the use of a *Myrica gale* plant for producing a herbicidal agent or for preparing a herbicidal composition, and also to the corresponding herbicidal compositions and the herbicidal compositions containing a newly demonstrated herbicidal agent.

19 Claims, 5 Drawing Sheets

USE OF A MYRICA GALE PLANT FOR PRODUCING A HERBICIDE AGENT

The present invention relates to the technical field of herbicides. More specifically, the present invention relates to the use of a *Myrica gale* plant for producing a herbicidal agent or for preparing a herbicidal composition, and also to the corresponding herbicidal compositions and the herbicidal compositions containing a newly demonstrated herbicidal agent.

The Myricaceae are, in view of the paleobotanical data, very certainly the oldest family of actinorhizal plants and are thought to have appeared at the Cenomanian during the upper Cretaceous series (96 million years) (Eriksson O. and Bremer B. 1992, Pollination systems, dispersal modes, life forms, and diversification rates in angiosperm families. Evolution 46: 333). More than 50 species belong to this family; however, the intrafamilial taxonomy has caused botanists many difficulties and two hypotheses, regarding the number of genera within this family, have been debated for more than a century, in particular as regards the taxonomic rank that should be given to *Myrica gale* (Wilbur R. L. 1994, The Myricaceae of the United States and Canada: genera, subgenera, and series. SIDA 16: 93; and Gleason H. A. and Cronquist A. 1991, Manual of vascular plants of northeastern United States and adjacent Canada. 2$^{nd}$ Edition. New York Botanical Garden, Bronx, pp 80-81 in particular). Recently, the studies by Huguet et al., 2005 (Huguet V. Gouy M. Normand P. Zimpfer J. F. and Fernandez M. P. 2005, Molecular Phylogeny of Myricaceae: a reexamination of host-symbiont specificity. Molec. Phylo. Evol. 34: 557) confirmed that the *Myrica gale* genus was a genus in its own right of the family Myricaceae, alongside the *Comptonia* genus and the *Morella* genus.

The *Myrica gale* genus (also called *Myrica gale*), which has the greatest geographical distribution, is described for certain therapeutic properties both in North America and in Europe (Sylvestre M. Legault J. Dufour D. and Pichette A. 2005, Chemical composition and anticancer activity of leaf essential oil of *Myrica gale* L. Phytomedicine 12: 299). Infusions of its leaves are used for the treatment of gastric disorders and cardiac difficulties (Svoboda K. P. Inglis A. Hampson J. Galambosi B. Asakawa Y. 1998, Biomass production, essential oil yield and composition of *Myrica gale* L. harvested from wild populations in Scotland and Finland. Flay. Frag. 13: 367). Essential oil of *Myrica gale* leaves is used in aromatherapy for its mucolytic and anticatarrh action in the case of respiratory problems (Bremness, L. (Ed) 1996 L'oeil Nature: Les plantes aromatiques et médicinales [Nature's eye: Aromatic and medicinal plants]. Bordas, Paris). This essential oil also appears to have abortive properties and is also used as an insect repellant in Scandinavia (Svoboda et al., 1998; Jaenson T. G. T. Palsson K. and Borg-Karlson A. K. 2005 Evaluation of extracts and oils of tick-repellent plants from Sweden Med. Vet. Entomol. 19: 345). Moreover, the leaves and fruits of *Myrica gale*, which are very aromatic and covered with glandular cells, are used as spices for flavoring beverages, soups and beer (Behre, K. E. 1999 The history of beer additives in Europe-a review. Vegetation History and Archaeobotany, 8, 35).

Document U.S. Pat. No. 4,309,207 describes the use of aerial parts of plants of the *Myrica* or *Vaccinium* genus for their antifungal or plant-growth-inhibiting activity. Since the publication of this US patent, which dates from 1982, there has been a reclassification within the family Myricaceae. The *Myrica* described in this document, and in particular *Myrica pensylvanica* which is the subject of example 4 of this document, have now been reclassified in the *Morella* genus, and this plant is now called *Morella pensylvanica*, as mentioned in the publication by Huguet et al. from 2005 mentioned above. In addition, there is a large physiological and genetic difference between *Myrica gale* plants and plants of the *Morella* genus, and in particular *Morella pensylvanica* (ex *Myrica pensylvania*). First of all, *Myrica gale* plants have a very specific interaction with bacteria. In addition, the inventors have demonstrated that these various plants (*Myrica gale* and *Morella*) express different active ingredients and exhibit very different phenolic-derivative profiles. Consequently, a herbicidal activity of plants of the *Morella* genus can in no way suggest a herbicidal activity of *Myrica gale*.

In the context of the invention, and completely unexpectedly, the inventors have demonstrated that *Myrica gale* plants, in the form of a crude part of a plant or of extracts, exhibit a phytotoxic activity and can consequently be used, as such, as bioherbicides or else for producing bioherbicides.

In this context, the subject of the present invention is the use of a *Myrica gale* plant for preparing a herbicidal composition.

According to one particular embodiment, an extract of a *Myrica gale* plant is prepared and incorporated into the herbicidal composition. The extract used is, for example, derived from the roots, the leaves, the stems, the fruits, the seeds and/or the flowers. Advantageously, the extract used is derived from the leaves, the fruits or the seeds. The extract used can, in particular, be obtained by extraction with a solvent selected from water, alcohols, ketones, esters, ethers, polyols, chlorinated solvents and mixtures of at least two of the abovementioned solvents.

In the context of the invention, the inventors have prepared extracts rich in flavonoids and derivatives.

According to another of its aspects, the invention relates to the use of a *Myrica gale* plant for producing a herbicidal agent. According to the steps carried out, the herbicidal agent may be in an isolated or purified form or as a mixture in a *Myrica gale* extract. The herbicidal agent produced is, in particular, selected from: myrigalone A, myrigalone E, myrigalone B, uvangoletin, demethoxymatteucinol, myrigalone D, demethoxymatteucinol-7-methyl ether and 2',4',6'-trihydroxy-3',5'-dimethyldihydrochalcone, compounds of which the inventors have demonstrated the herbicidal activity in the fruit extracts produced.

The subject of the invention is also herbicidal compositions comprising a *Myrica gale* extract, and also herbicidal compositions comprising a compound selected from: the herbicidal agent is selected from: myrigalone A, myrigalone E, myrigalone B, uvangoletin, demethoxymatteucinol, myrigalone D, demethoxymatteucinol-7-methyl ether and 2',4',6'-trihydroxy-3',5'-dimethyldihydrochalcone.

The extract used in the context of the invention is a cellular extract or an extracellular extract (leaching of leaves, for example) of the plant, which can be prepared according to any method known to those skilled in the art for extracting compounds from plant tissues. The extract can be obtained from the roots, the leaves, the stems, the fruits, the seeds and/or the flowers. Advantageously, the extract will be derived from the leaves, the fruits or the seeds, the use of which does not lead to the death of the plant from which they are extracted. Furthermore, the extracts of the leaves and of the fruits are particularly active.

By way of examples of extraction methods, mention may be made of the conventional methods of hot solvent extraction or cold solvent extraction, maceration, lixiviation, cryoextraction, digestion, decoction, extractions with supercritical $CO_2$, alone or as a mixture with a cosolvent, or extractions using undulator radiation, such as microwaves or ultrasound.

These methods can be combined with a subsequent purifying, filtering, concentrating and/or drying step.

Advantageously, the extract used is obtained by extraction with a solvent selected from water, alcohols, alkanes, ketones, esters, ethers, polyols, chlorinated solvents and mixtures of at least two of the abovementioned solvents. In particular, the extraction may be carried out using a solvent, such as an alcoholic solvent selected from ethanol or methanol or else polyethylene glycol or chloroform. A solvent as mentioned above is particularly preferred for extraction from the leaves, the flowers and the fruits of the plant. In the case of a solvent extraction, for example, it is possible to proceed in the following way: the selected part of the plant is harvested. This part of the plant, the extract of which is desired, which can be in fresh or dry form, is ground and/or shredded, optionally in the selected solvent, and then left to macerate, preferably with stirring, in the solvent, preferably for 1 hour to 30 days. Advantageously, a mass ratio of the part of the plant to the solvent of between 1/1 and 1/10 (m/m) will be used. The extraction can be carried out at a temperature of between −10 and 70° C., and in particular between 18 and 60° C. or at the reflux of the extraction solvent used. The extraction can also be carried out by lixiviation.

The extract obtained can then be concentrated, or dried, for example by evaporation or lyophilization. The extract obtained can be incorporated as it is into the composition or else be purified, treated or fractionated, so as to enrich for desired active ingredient. In particular, the extract used will be rich in flavonoids, and may in particular contain one or more compounds selected from myrigalone A, myrigalone E, myrigalone B, uvangoletin, demethoxymatteucinol, myrigalone D, demethoxymatteucinol-7-methyl ether and 2',4',6'-trihydroxy-3',5'-dimethyldihydrochalcone.

The *Myrica gale* extracts or directly the compounds above, preferably obtained from *Myrica gale* plants, and in particular from the fruits, can be used for preparing herbicidal compositions. Myrigalone A, myrigalone E, myrigalone B, uvangoletin, demethoxymatteucinol, myrigalone D, demethoxymatteucinol-7-methyl ether and/or 2',4',6'-trihydroxy-3',5'-dimethyldihydrochalcone obtained by chemical synthesis, or obtained from the *Myrica gale* plant, exhibit a herbicidal activity and can be used as herbicidal agent. The desired herbicidal activity may be the sort to inhibit seed germination, to prevent the resumption of underground or aerial meristem and bud development, or to inhibit the development and growth of the roots and also of the hypocotyls, the epicotyls and any aerial parts of the plants.

Any type of known herbicidal composition may be prepared. Use may in particular be made of herbicidal compositions in the form of granules, liquids, aqueous emulsions or emulsifiable concentrates, as adjuvants for herbicidal mixture. In adjuvants for herbicidal mixture, the crude part of *Myrica gale*, one of its extracts or one of the abovementioned herbicidal agents may be combined with one or more compounds selected from: ammonium sulfate, petroleum oil, esterified rapeseed oil, ethoxylated tallow fatty amine, paraffin mineral oil, polyethoxylated nonylphenol, *Laminaria digitata*, fatty amine polymer, polysorbate 20, pine oil, plant fatty acid derivatives, terpene alcohols, oleic acid, fatty acid methyl esters, polyoxyalkylated fatty alcohol phosphate esters, polyoxyethylene amine, alkyl polysaccharides, soybean lecithin, octyiphenol octaglycol ether, sulfuric ester, sulfonated fatty alcohols and acids, triethanolamine, ethylene/propylene complex polymer, polyalkylene oxide-modified heptamethyltrisiloxane, alkyl phenol, polyoxyethylene, modified heptamethyltrisiloxane, polyalkylene oxide, ethylene oxide, commonly used in adjuvants for herbicidal mixture, as shown in the list published by the French Ministry of Agriculture and Fisheries on the site http://e-phy.agriculture.gouv.fr/usa/31651003.htm to which reference may be made. The herbicidal compositions may also be incorporated into impregnated fabrics or polymer films.

The compositions will, for example, be used in such a way as to have concentrations, at the time of treatment, ranging from $10^{-12}$ to $10^2$ M, preferably from $10^{-5}$ to $10^0$ M of active herbicidal agent. In the case of compositions in the form of granules in particular, it will then be necessary to add water.

The examples hereinafter, with reference to the appended figures, make it possible to illustrate the invention, but are in no way limiting in nature.

FIG. 2 gives the NMR data of the compounds isolated.

Plant Material

The *Myrica gale* fruits were harvested along Lake Biscarosse in Gironde in December 2004. The ultrasound-assisted extraction by leaching of 350 g of dry fruits in 2 l of methanol made it possible to obtain 35 g of dry residue. The extract is resinous at ambient temperature.

Fractionation and Purification

Analytical Systems and Detection

After each step of the purification, the fractions obtained are analyzed on various chromatographic systems, TLC and HPLC, in order to determine their composition and to combine those which are qualitatively homologs. The fractions combined, considered to be of value, are stored for the subsequent work and are then the subject of the perfecting of new separation systems.

At each fractionation step, the developing and the visualizing of the TLC plates uses UV irradiation at 254 and 366 nm.

The HPLC analyses are carried out on an Agilent 1100, the Kromasil column (250×4.6 mm, 5 µm, 100 Å) consisting of C18 grafted silica. The volume of sample injected into the column is 5 µl, with UV detection between 200 and 700 nm by means of a diode array detector. Four particular wavelengths are used for visualizing the chromatograms: 254, 280, 320 and 350 nm. The elution solvent is a gradient of acetonitrile in water with 0.4% of acetic acid.

Preparative Systems

Figure 1:
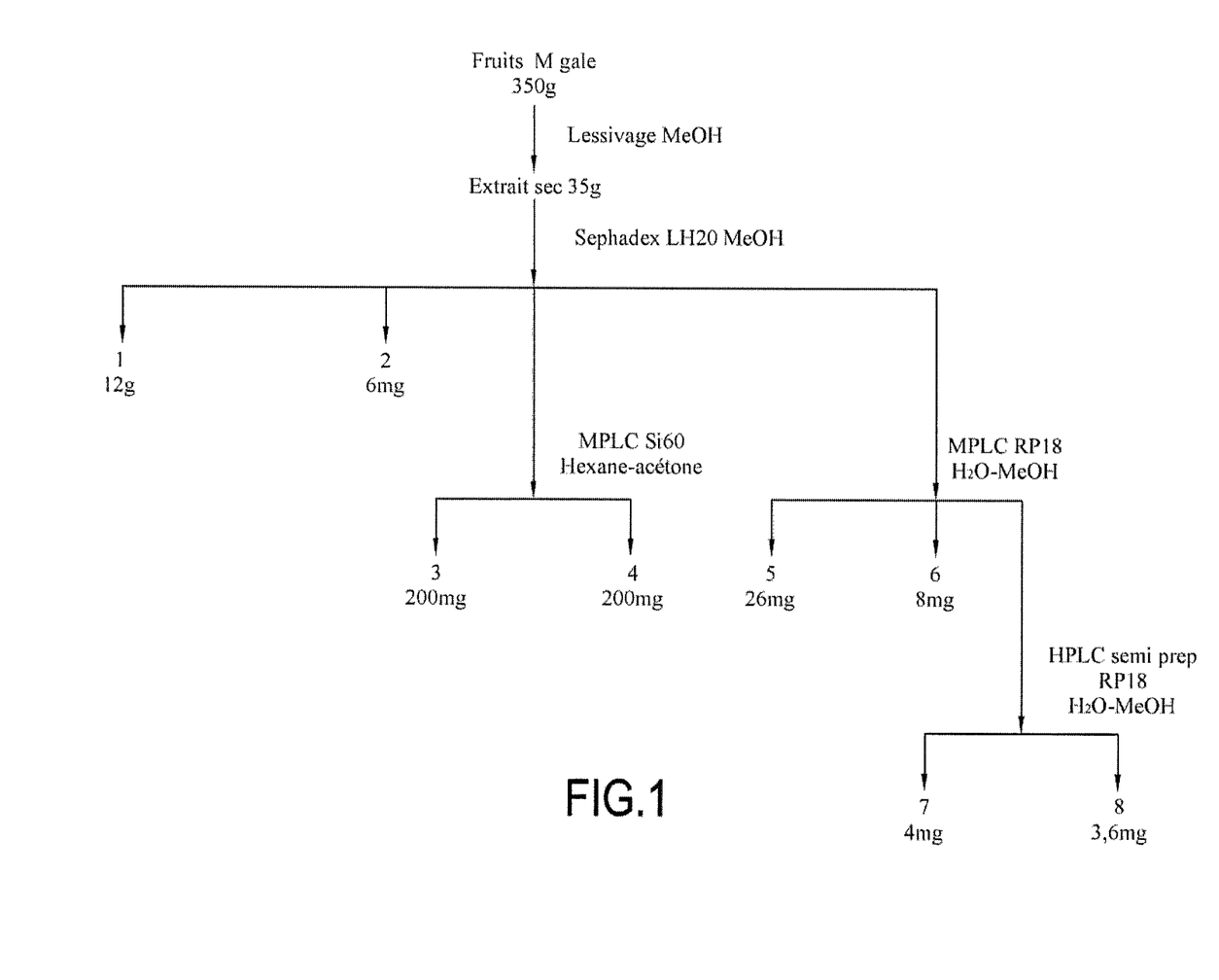
FIG. 1 summarizes the fractionation protocol used.

The fractionation protocol is summarized in FIG. 1, on which the fractions which do not give rise to the production of any pure molecule are not represented.

The *Myrica gale* fruit leachate is fractionated by means of a first chromatography on an open column of Sephadex LH-20 (600×45 mm) with an elution solvent consisting of methanol. This partition makes it possible to recover 13 fractions (A to M).

The analysis of fraction C showed that it consisted only of one molecule, compound 1, in an amount of 12 g. Compound 2 (6 mg) was obtained following crystallization thereof from fraction D at −20° C. The fractions of greater masses (E, 8 g and F, 7 g) were subsequently subjected to additional chromatographies. An MPLC (450×25 mm) of fraction E on silica 60 (15×40 µm), with an elution solvent consisting of a gradient of acetone in hexane, made it possible to obtain 2 pure molecules (3, 200 mg and 4, 100 mg). The 13 fractions FA to FM were obtained by chromatography of fraction F by reverse phase (RP18 15×40 μm) MPLC (450×25 mm). Two of these fractions each consisted of one pure molecule (compounds 5, 26 mg and 6, 8 mg). Fraction FL was subjected to a reverse-phase semi-preparative HPLC (X-Terra Prep MS C18, 5 μm, 10×100 mm, isocratic 40% of solvent A ($H_2O$) 60% of solvent B (acetonitrile), flow rate 3 ml/min). This final chromatography made it possible to purify compounds 7 and 8 (4 and 3.6 mg).

Structural Analyses

The structural elucidation of the compounds was established by interpretation of the data from UV spectroscopy, mass spectrometry and $^1H$ and $^{13}C$ one-dimensional NMR and also $^1H$—$^{13}C$ HSQC and $^1H$—$^{13}C$ HMBC heteronuclear two-dimensional NMR. The UV spectra were recorded on a UVIKON 943 instrument in methanol. The mass spectra were carried out on an Agilent 1100 LC-MS system equipped with an MSD 1100 detector and a positive and negative APCI interface. The NMR spectra were carried out in the communal NMR department of the UCBL [University Claude Bernard Lyon] on a Bruker DRX500 instrument in methanol-$d_4$ at 500.13 MHz in proton NMR and 125.77 MHz in carbon-13 NMR.

The various successive chromatography steps carried out on the *Myrica gale* fruit leachate made it possible to purify and identify 8 metabolites. The structures of these compounds are the following:

2: $R_2' = OH$, $R_3' = CH_3$, $R_4' = OCH_3$, $R_5' = H$, $R_6' = OCH_3$
3: $R_2' = R_6' = OH$, $R_3' = R_5' = CH_3$, $R_4' = OCH_3$
4: $R_2' = R_4' = OH$, $R_3' = R_5' = H$, $R_6' = OCH_3$
5: $R_2' = R_4' = R_6' = OH$, $R_3' = R_5' = CH_3$

6: $R_7 = OH$
8: $R_7 = OCH_3$

The structural elucidations were established by interpretation of the proton and carbon NMR data, respecting the correlations observed in HMBC (FIG. 2). The tables present in FIG. 2 give the values of the $^1H$ and $^{13}C$ NMR shifts of the chalcones and dihydrochalcones (A) and of the flavanones (B). The shifts are given in ppm, the coupling constants between parentheses are in Hz. All the molecules purified are flavonoids. All the proposed formulae are coherent with all of the other spectral data, namely UV and mass spectrometry data.

All the compounds had already been described in the literature. Of the 8 molecules purified, 5 had already been identified in *Myrica gale* and have the following names: myrigalone A, E and B, for compounds 1, 2 and 3 respectively, myrigalone D for compound 7, and uvangoletin for compound 4. The following other compounds have never been described in *Myrica gale*: demethoxymatteucinol for compound 6, demethoxymatteucinol-7-methyl ether for compound 8. Finally, 2',4',6'-trihydroxy-3',5'-dimethyldihydrochalcone for compound 5 had never been described as a natural substance.

Bioherbicidal Activity of *Myrica gale*

Materials and Methods

Plant extracts used for evaluating their herbicidal activity:

The following extracts were tested with regard to their herbicidal properties:
  dry leaves reduced to powder
  dry whole fruits
  methanolic fruit leachate
  pure myrigalone A in methanolic solution.

Plants Used as Target for the Herbicidal Activity

The following plants were used for evaluating the herbicidal activity of the various *Myrica gale* extracts:
  sorghum
  wheat
  mustard
  watercress
  knotweed.

Phytotoxicity Activity Tests

The seeds of the target plants are placed at the surface of a filter paper (Whatman No. 1) in a Petri dish (9 cm in diameter). Depending on the target plants, the number of seeds per Petri dish ranges from 8 to 15 seeds.

8 ml of water are added to the Petri dish in order to ensure germination of the target seeds.

The various *Myrica gale* methanolic extracts to be tested are introduced into these 8 ml of water at concentrations of 0.1 mg/ml, 0.5 mg/ml or 1 mg/ml, provided by 50 μl of methanol. The controls consist of methanol.

For the evaluations of the activities of the dry extracts (ground material of leaves and whole fruits), the extracts are sprinkled at the surface of the Petri dishes, at concentrations of 10 mg/ml, 20 mg/ml or 30 mg/ml. The controls are not sprinkled.

All the conditions tested are repeated at least 3 times (3 Petri dishes per treatment, each containing from 8 to 15 seeds). The experiments were reproduced independently several times.

After the addition of the various extracts to be tested, the Petri dishes are placed at 28° C.

The dishes are read as soon as the controls have suitably grown, before the 1-leaf stage.

Parameters Measured for the Herbicidal Evaluation

After germination of the target seeds, the lengths of the roots and of the hypocotyls of each plantlet are measured, as is the degree of seed germination.

Results

Figure 3:
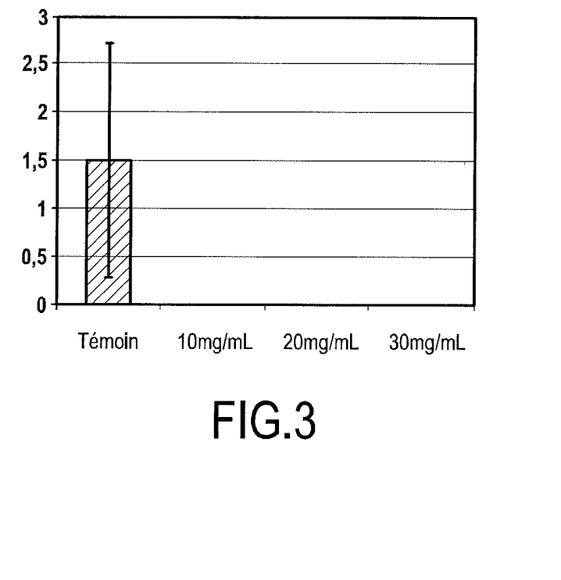
FIGS. 3 to 6 give the average lengths (cm) of mustard roots in the presence, respectively, of various amounts of ground materials derived from *Myrica gale* leaves, of whole *Myrica gale* seeds, of methanolic leachate of *Myrica gale* seeds, and of myrigalone A in methanolic solution.

FIG. 3 gives the average lengths (cm) of mustard roots in the presence of 10, 20 and 30 mg/ml of ground materials derived from *Myrica gale* leaves. There is complete inhibition of plantlet development from 10 mg/ml.

Figure 4:
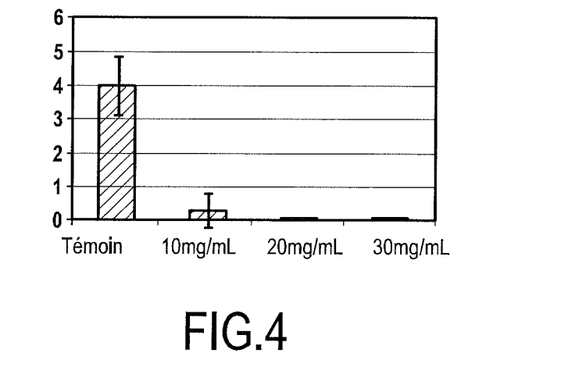

FIG. 4 gives the average lengths (cm) of watercress roots in the presence of 10, 20 and 30 mg/ml of whole *Myrica gale* seeds.

Figure 5:
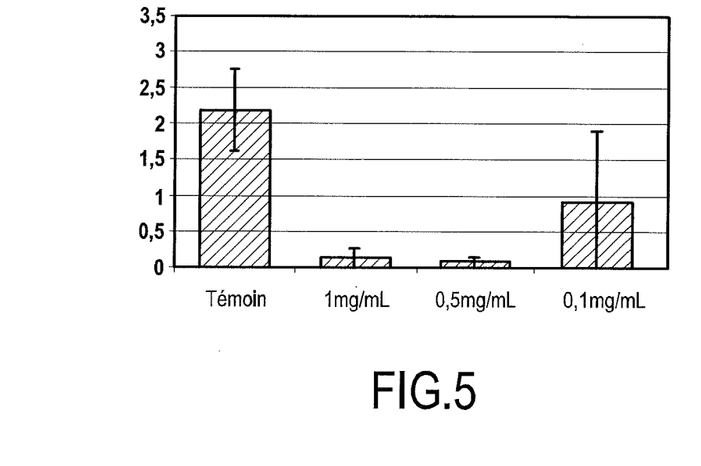

FIG. 5 gives the average lengths (cm) of mustard hypocotyls in the presence of 0.1, 0.5 and 1 mg/ml of methanolic leachate of *Myrica gale* seeds.

Figure 6:
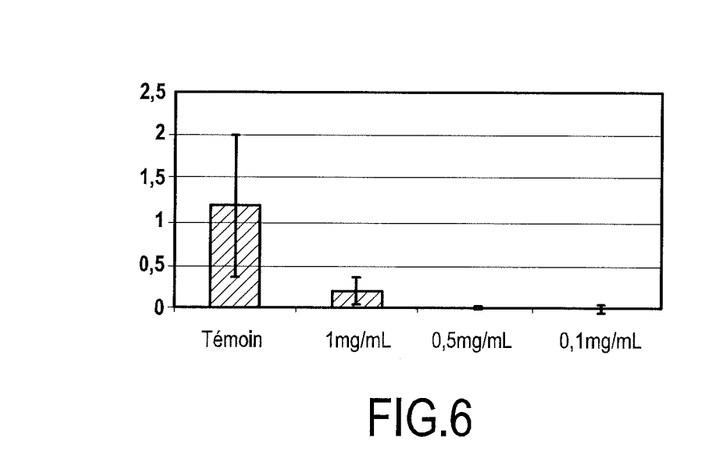

FIG. 6 gives the average lengths (cm) of mustard seeds in the presence of 0.1, 0.5 and 1 mg/ml of myrigalone A in methanolic solution.

Analysis of the Variability of the Phenolic Compounds Produced in the Various Organs of the Plant by *Myrica gale* and Two Species with Broad Nodulation Spectrum, *Morella cerifera* and *Morella pensylvanica*

1—Plant Material

The inter- and intraspecific variability analyses were carried out on leaves, roots and seeds taken from adult plants of the *Myrica gale, Morella cerifera* and *Morella pensylvanica* species. Two types of material were used. The 1st type concerns 12- to 18-month-old nodulated plants cultured out of soil under controlled conditions (Huguet, 2003). The samples of leaves and roots derived from these plants were stored at ambient temperature after drying in the dark and in the open air. The 2nd type of material concerns adult field plants, the leaf and root samples of which are stored at −20° C. without having been dried (Table 2).

2—Preparation of Plant Extracts 2-1—Leaf and Seed Exudates

The compounds present at the surface of the leaves and of the seeds are recovered by leaching of the samples in 40 ml of an ethanol/methanol (1:1) mixture at ambient temperature for 20 minutes, with stirring. The solvent is then evaporated to dryness under reduced pressure and the residue obtained is then taken up in 1.5 ml of methanol.

2-2—Content of the Leaves, Roots, Seeds and Plantlets

The samples are ground in liquid nitrogen, and the cellular compounds are then hot-extracted in 50 ml of de methanol/ethanol (1/1) by refluxing for 2×15 minutes. After filtration, the solvent is evaporated to dryness under reduced pressure and the residue is taken up in 2 to 3 ml of methanol.

All the samples are stored at −20° C.

3—Analysis of Phenolic Compounds

The analysis of the various samples is carried out by HPLC chromatography. The instrument used is an Agilent 1100, the Kromasil column (250×4.6 mm, 5 μm, 100 Å) consisting of C18 grafted silica. The volume of sampling injected into the column is 20 μl. The gradient of the elution solvents for the analysis of the leachates is different than that for the analysis for the ground materials and is given in TABLE 1 below:

TABLE 1

Elution conditions used in HPLC

|  | Time (min) | Solvent A* | Solvent B+ |
|---|---|---|---|
| Foliar leachates | 0.00 | 70% | 30% |
|  | 10.00 | 70% | 30% |
|  | 40.00 | 25% | 75% |
|  | 50.00 | 15% | 85% |
|  | 55.00 | 15% | 85% |
|  | 60.00 | 10% | 90% |
|  | 66.00 | 10% | 90% |
|  | 69.00 | 70% | 30% |
| Ground materials | 0.00 | 85% | 15% |
|  | 8.00 | 85% | 15% |
|  | 18.00 | 69% | 31% |
|  | 24.00 | 69% | 31% |
|  | 38.00 | 22% | 78% |
|  | 46.00 | 22% | 78% |
|  | 54.00 | 15% | 85% |
|  | 58.00 | 15% | 85% |
|  | 61.00 | 85% | 15% |

Solvent A* For the leachates: $H_2O$/HCOOH (100/4)
For the ground materials: $H_2O$/HCOOH (100/2)
Solvent B+ For the leachates: acetonitrile/$H_2O$/HCOOH (80/20/4)
For the ground materials: acetonitrile/$H_2O$/HCOOH (80/20/2)

The diode array detector makes it possible to carry out detection at all the wavelengths of the UV-Visible spectrum. Three wavelengths were therefore used to monitor the analyses: 280, 320 and 350 nm. In addition, this detector performs an absorption spectrum every 30 ms and therefore makes it possible to assign to each (sufficiently intense) signal, on exiting the column, its UV absorption spectrum.

4—Statistical Analysis

The results of the HPLC are recorded in a matrix of binary data (1/0) with x columns (chromatogram peaks) and y rows (samples). This matrix is then analyzed by AFC analysis. These statistical tests are carried out with the ADE4 software (www.pbil.univ-lyon1.fr).

5—Results

Since the gradient of the elution solvent used for the HPLC analyses of the foliar leachates is different than that used for the ground materials, comparison of the retention times between these two types of sample is not possible and their chromatographic profiles are therefore analyzed separately.

The comparison of the chromatograms is carried out at two detection wavelengths: 280 nm which makes it possible to observe the phenolic compounds in general, and 350 nm which corresponds to the absorbance more specific for flavonoids.

5-1—Foliar Leachates and Foliar and Root Ground Materials

The AFC analysis of the chromatograms of the foliar leachates and ground materials and of the root ground materials systematically separates, on the first axis, the *Myrica gale* samples from those of the other two species (FIG. 5). This dichotomy is observed at both of the detection wavelengths used, 280 and 350 nm.

Figure 7:
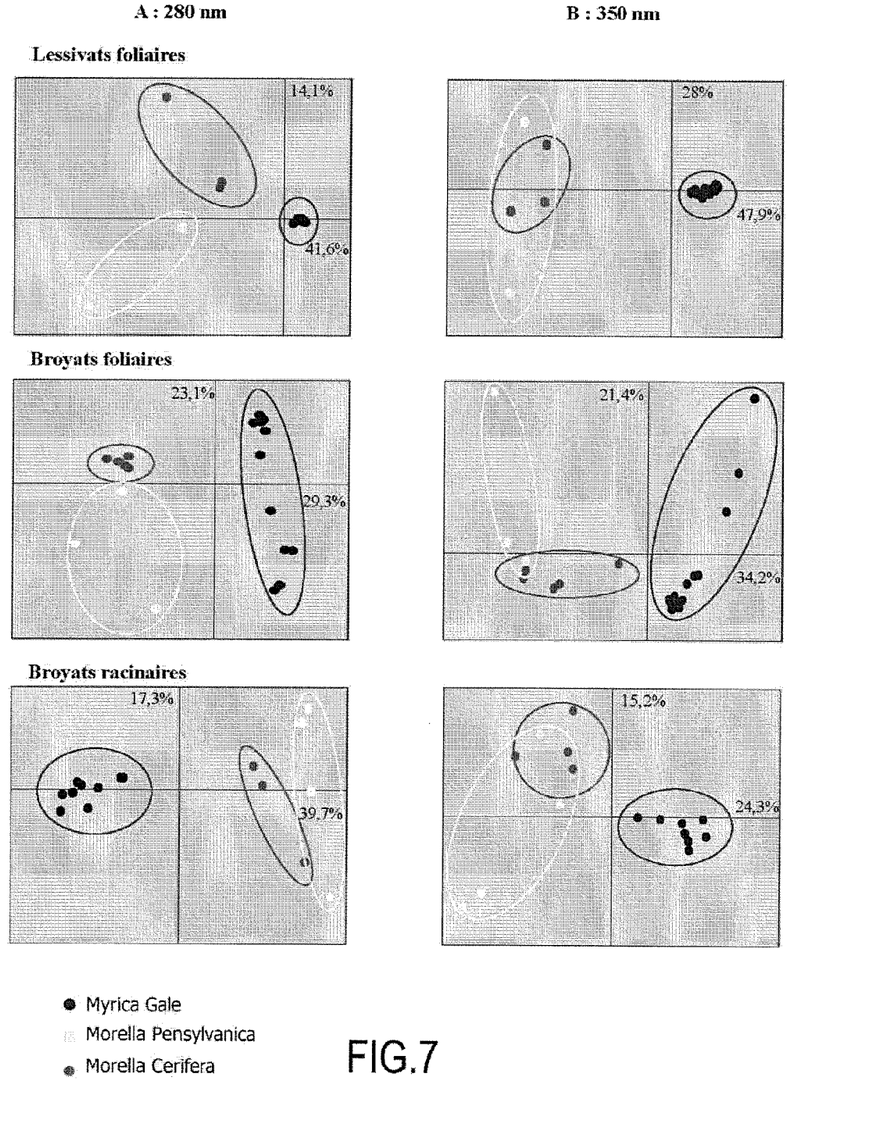
FIG. 7 gives chromatograms demonstrating the very clear differences in terms of chemical content, of *Myrica gale* extract compared with *Morella cerifera* and *Morella pensylvanica* extracts and *Myrica gale* extracts and identification of the metabolites.

Only the AFCs derived from the signals of the foliar ground materials make it possible to separate, on the second axis and especially at the two detection wavelengths, the *Morella cerifera* samples from those of *Morella pensylvanica* (FIG. 7).

The number of signals detected in the foliar and root ground materials is substantially the same for the three species studied. On the other hand, approximately twice as many signals are detected in the *Myrica gale* foliar exudates than in those of the other two species.

In these three compartments (foliar leachates and ground materials and root ground materials), the *Myrica gale* samples exhibit two to three more signals which are specific thereto than *Morella cerifera* and *Morella pensylvanica* do.

5-2—Seed Ground Materials and Leachates

The chromatographic profiles of the ground material derived from *Myrica gale* seeds are visually extremely different than those of the ground materials derived from *Morella pensylvanica* and *Morella cerifera* seeds; in particular, the strength and the number of the most lipophilic signals are higher in *Myrica gale*. The ground material derived from *Myrica gale* seeds is very rich in secondary metabolites, with more than a hundred or so signals detected, 37% of which are absent from the extracts of seeds from the other two species. Among these specific peaks, about twelve are located at the end of the chromatogram (starting from 45 minutes), corresponding to the most lipophilic molecules of the extract. The UV spectra of the peaks specific to *Myrica gale* reveal a very large diversity of compounds, including phenolic acids, flavonoids and also compounds with atypical spectra. Since only one origin of the seeds of each species is available, no statistical analysis was carried out.

In conclusion, the HPLC analyses carried out on all the samples of the various organs and compartments show that the three species studied produce a very large diversity of metabolites with the presence of several tens of signals detected.

The analyses of qualitative variability of phenolic compounds separate, on the first axis of all the AFC analyses, the *Myrica gale* samples from those of the two species with broad nodulation spectrum, *Morella cerifera* and *Morella pensylvanica*. This separation is systematically correlated with tens of peaks on the chromatograms of the extracts. It therefore appears that *Myrica gale* can be distinguished from these two species by virtue of an original phenolic content.

The invention claimed is:

1. A method of obtaining phytotoxic activity by applying on a seed of a plant, a composition having one or more compounds found in the *Myrica gale* plant in an amount effective to obtain phytotoxic activity comprising inhibiting seed germination, preventing the resumption of underground or aerial meristem and bud development, or inhibiting the development and growth of the roots, the hypocotyls, the epicotyls, the plantlets or aerial parts of the plant.

2. A method according to claim 1 wherein the composition is obtained from a *Myrica gale* plant.

3. A method according to claim 1 wherein the composition contains an extract of a *Myrica gale* plant.

4. A method according to claim 1 wherein the composition contains an extract of a *Myrica gale* plant derived from the roots, the leaves, the stems, the fruits, the seeds and/or the flowers of the *Myrica gale* plant.

5. A method according to claim 1 wherein the composition contains an extract of a *Myrica gale* plant derived from the leaves, the fruits or the seeds of the *Myrica gale* plant.

6. A method according to claim 1 wherein the composition contains an extract of a *Myrica gale* plant obtained by extraction from the roots, the leaves, the stems, the fruits, the seeds and/or the flowers of the *Myrica gale* plant with a solvent selected from water, alcohols, ketones, esters, ethers, polyols, chlorinated solvents and mixtures of at least two of the solvents.

7. A method according to claim 1 wherein the composition contains an extract of a the *Myrica gale* plant rich in flavonoids.

8. A method according to claim 1 wherein the one or more compounds found in the *Myrica gale* plant is in an isolated and purified form or as a mixture in a *Myrica gale* extract in an amount effective to obtain phytotoxic activity comprising inhibiting seed germination, preventing the resumption of underground or aerial meristem and bud development, or inhibiting the development and growth of the roots, the hypocotyls, the epicotyls, the plantlets or aerial parts of an plant.

9. A method according to claim 1 wherein the one or more compounds found in the *Myrica gale* plant in an amount effective to obtain phytotoxic activity comprising inhibiting seed germination, preventing the resumption of underground or aerial meristem and bud development, or inhibiting the development and growth of the roots, the hypocotyls, the epicotyls, the plantlets or aerial parts of the plants, is selected from: myrigalone A, myrigalone E, myrigalone B, uvangoletin, demethoxymatteucinol, myrigalone D, demethoxymatteucinol-7-methyl ether and 2',4',6'-trihydroxy-3',5'-di methyldihydrochalcone.

10. A *Myrica gale* extract, myrigalone A, myrigalone E, myrigalone B, uvangoletin, demethoxymatteucinol, myrigalone D, demethoxymatteucinol-7-methyl ether or 2',4',6'-trihydroxy-3',5'-dimethyldihydrochalcone, in contact with a plant seed, present in an effective amount to obtain phytotoxic activity that comprises inhibiting seed germination, preventing the resumption of underground or aerial meristem and bud development, or inhibiting the development and growth of the roots, the hypocotyls, the epicotyls, the plantlets or aerial parts of a plant upon contact with the plant seed.

11. A *Myrica gale* extract according to claim 10 wherein the extract is derived from the roots, the leaves, the stems, the fruits, the seeds and/or the flowers of a *Myrica gale* plant.

12. A *Myrica gale* extract according to claim 10 wherein the extract is obtained by extraction from the roots, the leaves, the stems, the fruits the seeds and/or the flowers of the *Myrica gale* plant with a solvent selected from water, alcohols, ketones, esters, ethers, polyols, chlorinated solvents and mixtures of at least two of the solvents.

13. A *Myrica gale* extract according to claim 10 wherein the extract comprises one or more compounds selected from myrigalone A, myrigalone E, myrigalone B, uvangoletin, demethoxymatteucinol, myrigalone D, demethoxymatteucinol-7-methyl ether and 2',4',6'-trihydroxy-3',5'-di methyldihydrochalcone.

14. A composition, in contact with a plant seed, containing a *Myrica gale* extract, myrigalone A, myrigalone E, myrigalone B, uvangoletin, demethoxymatteucinol, myrigalone D, demethoxymatteucinol-7-methyl ether or 2',4',6'-trihydroxy-3',5'-dimethyldihydrochalcone in an effective amount to obtain phytotoxic activity upon contact with the plant seed that involves inhibiting seed germination, preventing the resumption of underground or aerial meristem and bud development, or inhibiting the development and growth of the roots, the hypocotyls, the epicotyls, the plantlets or aerial parts of a plant, wherein the composition also contains one or more compounds selected from: ammonium sulfate, petroleum oil, esterified rapeseed oil, ethoxylated tallow fatty amine, paraffin mineral oil, polyethoxylated nonylphenol, *Laminaria digitata*, fatty amine polymer, polysorbate 20, pine oil, plant fatty acid derivatives, terpene alcohols, oleic acid, fatty acid methyl esters, polyoxyalkylated fatty alcohol phosphate esters, polyoxyethylene amine, alkyl polysaccharides, soybean lecithin, octylphenol octaglycol ether, sulfuric ester, sulfonated fatty alcohols and acids, triethanolamine, ethylene/propylene complex polymer, polyalkylene oxide-modified heptamethyltrisiloxane, alkyl phenol, polyoxyethylene, modified heptamethyltrisiloxane, polyalkylene oxide and ethylene oxide.

15. A composition as claimed in claim 14, wherein the composition is in the form of granules, liquids, aqueous emulsions or emulsifiable concentrates.

16. A composition as claimed in claim 14, wherein the composition is incorporated into an impregnated fabric or a polymer film.

17. A composition as claimed in claim 14, wherein the composition contains a *Myrica gale* extract derived from the roots, the leaves, the stems, the fruits, the seeds and/or the flowers of a *Myrica gale* plant.

18. A composition as claimed in claim 14, wherein the composition contains a *Myrica gale* extract obtained by extraction from the roots, the leaves, the stems, the fruits the seeds and/or the flowers of the *Myrica gale* plant with a solvent selected from water, alcohols, ketones, esters, ethers, polyols, chlorinated solvents and mixtures of at least two of the solvents.

19. A composition as claimed in claim 14, wherein the composition contains a *Myrica gale* extract comprising one or more compounds selected from myrigalone A, myrigalone E, myrigalone B, uvangoletin, demethoxymatteucinol, myrigalone D, demethoxymatteucinol-7-methyl ether and 2',4',6'-tri hydroxy-3',5'-dimethyldihydrochalcone.

* * * * *